United States Patent [19]

Yamaguchi et al.

[11] Patent Number: 5,468,894
[45] Date of Patent: Nov. 21, 1995

[54] METHOD OF MANUFACTURING FSI(OR)$_3$

[75] Inventors: Ryuichi Yamaguchi; Koichi Kiso; Kiyoshi Tazuke; Hideaki Machida; Katsuhiro Mihirogi; Yukichi Takamatsu, all of Kanagawa, Japan

[73] Assignee: TRI Chemical Laboratory Inc., Kanagawa, Japan

[21] Appl. No.: 215,568

[22] Filed: Mar. 22, 1994

[51] Int. Cl.$^6$ .................................................. C07F 7/08
[52] U.S. Cl. ................................................... 556/477
[58] Field of Search .................................... 556/477

[56] References Cited

U.S. PATENT DOCUMENTS 2,436,777  2/1948  Fletcher et al. .......................... 556/477
3,408,380  10/1968 Pittman et al. ........................... 556/477
3,621,045  11/1971 Muller et al. ............................ 556/477

FOREIGN PATENT DOCUMENTS 586070  4/1993  Japan .

*Primary Examiner*—Paul F. Shaver
*Attorney, Agent, or Firm*—Oblon, Spivak, McClelland, Maier, & Neustadt

[57] ABSTRACT

By reacting Si(OR)$_4$ with HF, FSi(OR)$_3$ of high purity can be obtained easily and economically.

13 Claims, 2 Drawing Sheets

METHOD OF MANUFACTURING FSI(OR)$_3$

The present invention relates to a method of manufacturing trialkoxyfluorosilane FSi(OR)$_3$.

BACKGROUND OF THE INVENTION

In recent years, as the semiconductor industries and the ceramic industries has been advancing, demand for silicon compound as a main raw material in the industries has become great. The silicon compound, for example, such as silane [SiH$_4$], tetraalkoxysilane [Si(OR)$_4$], of which substituents are the same has been used broadly. Additionally, increase of demand for a compound such as trialkoxyfluorosilane also has become large.

By the way, for manufacture of trialkoxhalosilane [XSi(OR)$_3$] (where, X is chlorine, bromine or iodine) other than trialkoxyfluorosilane, a reaction of Si(OR)$_4$ and HX (where, X is chlorine, bromine or iodine) has been considered. In this reaction, however, a plurality of products such as X$_3$Si(OR), X$_2$Si(OR)$_2$, XSi(OR)$_3$ and Si(OR)$_4$ are produced. Moreover, the boiling points of these products are close each other, so that it was impossible to obtain a high purity product. By these reasons, adoption of the reaction of Si(OR)$_4$ and HF has never been considered to manufacture FSi(OR)$_3$, because it is considered that this case also has the same troublesome problems as above.

That is, it is only proposed for the methods of manufacturing FSi(OR)$_3$ using antimony compound or aluminum compound (J. Am. Chem. Soc., 68, 76(1946), Nature, 158, 672(1946), U.S. Pat. No. 3,374,247), for example:

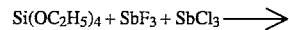

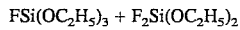

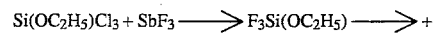

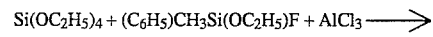

using complicated organic silicone compounds as starting materials, for example,

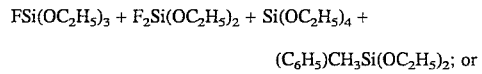

When using the above manufacture methods, however, it may occur that antimony or aluminum as a raw material mixes into the product as a metal impurity. Also, an antimony compound is a poisonoum substance, so that it is troublesome to handle it. Additionally, if this method is adopted for a production method in a factory, environmental conservation must be considered. Moreover, the complicated organic silicone compound such as (C$_6$H$_5$)CH$_3$SiF$_2$ or (C$_6$H$_5$)CH$_3$Si(OC$_2$H$_5$)F is expensive and difficult to obtain it, so that this method is not suitable for a factory production method.

SUMMARY OF THE INVENTION

An object of the present invention is to offer FSi(OR)$_3$ of high purity, which can be obtained easily and economically.

The object of the present invention is achieved by a method of manufacturing FSi(OR)$_3$ characterized in reacting Si(OR)$_4$ with HF.

More, it is achieved by a method of manufacturing FSi(OR)$_3$ characterized in purifying a product without delay after completion of reaction of Si(OR)$_4$ with HF.

More, in the present invention, it is desirable to react Si(OR)$_4$ with HF by blowing the HF into a liquid Si(OR)$_4$ having been cooled to not more than 0° C., especially desirable to react Si(OR)$_4$ with HF by blowing said HF of an amount larger than theoretical value into the liquid Si(OR)$_4$ having been cooled to not more than Further, it is desirable to heat the resulted solution to a temperature of a range from boiling point (19° C.) of HF to room temperature (25° C.) after completion of reaction of Si(OR)$_4$ with HF, then di-fluoride and unreacted substances are removed.

As an R in trialkoxyfluorosilane FSi(OR)$_3$, alkyl groups such as methyl group, ethyl group, propyl group, butyl group, pentyl group, C$_{12}$H$_{25}$—, C$_{14}$H$_{29}$— and C$_{16}$H$_{33}$—, phenyl group and alkylphenyl group (where, alkyl means CH$_3^-$, C$_2$H$_5^-$, C$_3$H$_7^-$, C$_4$H$_9^-$, C$_5$H$_{11}^-$, C$_{12}$H$_{25}^-$, C$_{14}$H$_{29}^-$ or C$_{16}$H$_{33}^-$) can be listed up.

Therefore additionally, as an R in Si(OR)$_4$ for a raw material, alkyl groups (methyl group, ethyl group, propyl group, butyl group, pentyl group, C$_{12}$H$_{25}$—, C$_{14}$H$_{29}$— and C$_{16}$H$_{33}$—), phenyl group and alkylphenyl group can be listed up.

By the present invention, it is not necessary to use a poisonoum substance such as an antimony compound. Additionally it enables easy to handle materials and control the reaction process, also metal impurities can not mix into the product. Moreover, as it enables to reduce material cost, this method is suitable to mass production. For example, it is possible to easily and economically obtain trialkoxyfluorosilane FSi(OR)$_3$ of high purity, more than 99.99%.

Next, the present invention is explained in details.

The present invention is achieved by successfully using the following chemical and physical nature:
(1) Using tetraalkoxysilane and HF as starting raw materials.
(2) It is enough to control the reaction temperature and flow rate of HF when reacting tetraalkoxysilane with HF, thus the reaction control is simple.
(3) Difluoride F$_2$Si(OR)$_2$ as a by-product is unstable and immediately inverted to trifluoride and monofluoride.
(4) The boiling point of trifluoride as a by-product is low, so that purifying the final product is easy.

Concretely speaking, tetraalkoxysilane Si(OR)$_4$ of 10 mol put in a reaction vessel was stirred intensely under a nitrogen gas current. After the Si(OR)$_4$ was cooled by ice, HF was blown into the reaction vessel under control of flow by a mass flow controller. And at every quantity of HF supply, the following points were examined, that is, produced quantity of trialkoxyfluorosilane FSi(OR)$_3$, consumed quantity of the starting raw material Si(OR)$_4$, produced quantity of alcohol and existence of trifluoride and difluoride. As the result, it was found that Si(OR)$_4$ of 10 tool and HF of 10 mol are used all and the expected quantity of FSi(OR)$_3$ was obtained. Furthermore unreacted HF and difluoride as a by-product were removed immediately by heating the reaction vessel without impairing FSi(OR)$_3$. With distilling the obtained compound, an extremely high purity of trialkoxyfluorosilane FSi(OR)$_3$ was obtained. Next, referring examples the present invention is explained.

EXAMPLES OF THE INVENTION

EXAMPLE 1

Figure 1:
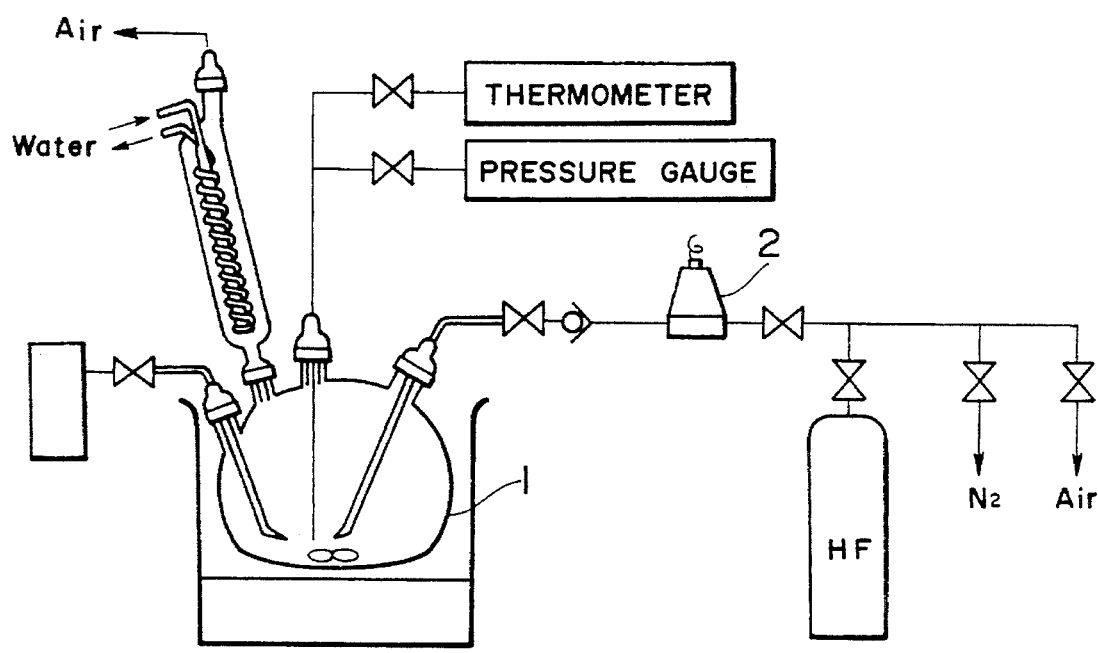
FIG. 1 illustrates an outline of the apparatus used for manufacturing FSi(OR)$_3$ of the present invention.

A device shown in FIG. 1 was prepared. And tetraethoxysilane 10 mol was added into the reaction vessel 1 and cooled off to −5° C., then HF was blown thereinto at a flow quantity 15seem, as being controlled by a mass flow controller 2. Thus, the following reaction was conducted.

Si(OC$_2$H$_5$)$_4$+HF→FSi(OC$_2$H$_5$)$_3$+C$_2$H$_5$OH.

Figure 2:
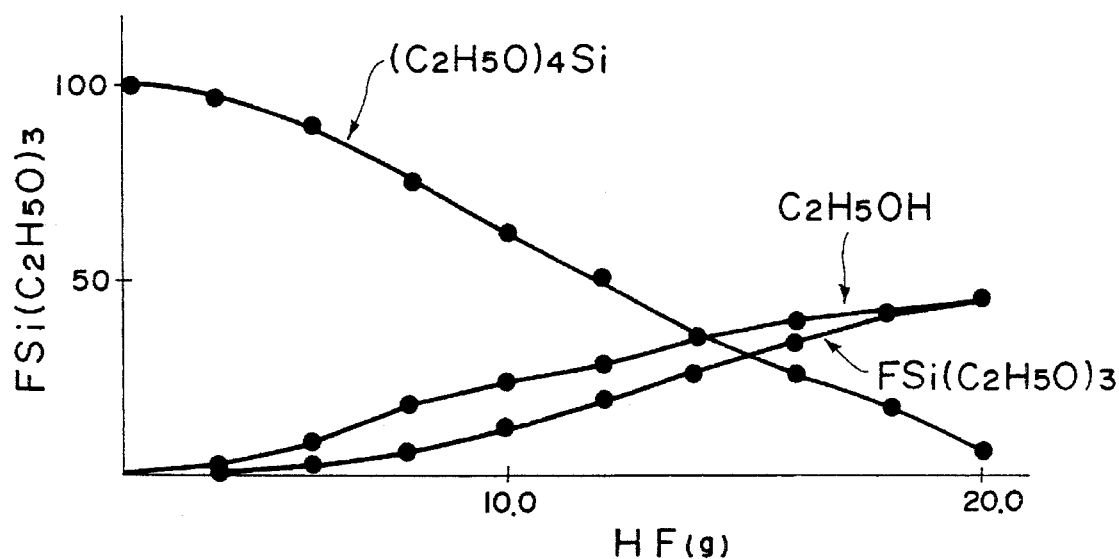
FIG. 2 is a graph showing the relation of quantity of HF supply and FSi(OR)$_3$.

After completion of reaction to remove unreacted HF, the reaction vessel was heated (in the range of temperature from not less than boiling point of HF to not more than room temperature). At each supply of HF of approximate 1 mol, sampling was carried out and the situation of reaction was traced using gas chromatography. A measurement result till HF 10 mol is consumed completely is shown in FIG. 2. According to the FIG. 2, it was found that HF was not detected and the products consisted of triethoxyfluorosilane and ethanol. It was desirable to set the HF supply quantity larger than a theoretical value because of partial thermal decomposition reaction.

Next, the refinement of triethoxyfluorosilane obtained as above was carried out. That is, after removing ethanol under reduced pressure of 400 torr using a general refinement distillation device triethoxyfluorosilane was distilled under reduced pressure of 200 torr, and purity of the product was analyzed. As a result, the yield of product was 90%, and it agreed with the result that shown in FIG. 2.

A Frame/Zeeman atomic absorption photometer was used to measure metal impurities in the above product and it was found that the content of each metal element (Co, Cr, Cu, Fe, Ni, Mn, Zn, Pb, Na, K, Ca, Mg) was under limitation of detection (<0.1 ppm), thus purity of the product was so high. More, the result of element analysis showed that C:71.9%, H:15.7%, F:20.1%, Si:28.0% and it agreed with the theoretical value of triethoxyfluorosilane, (FSi(OC$_2$H$_5$)$_3$), that is C:72.07%, H:16.20%, F:19.00%, Si:28.09%.

EXAMPLE 2

A device shown in FIG. 1 was prepared. And tetramethoxysilane 10 mol was added into the reaction vessel 1 and cooled off to −5° C., then HF was blown thereinto at a flow quantity 15 seem, as being controlled by a mass flow controller 2. Thus, the following reaction was conducted.

Si(OCH$_3$)$_4$+HF→FSi(OCH$_3$)$_3$+CH$_3$OH.

Figure 3:
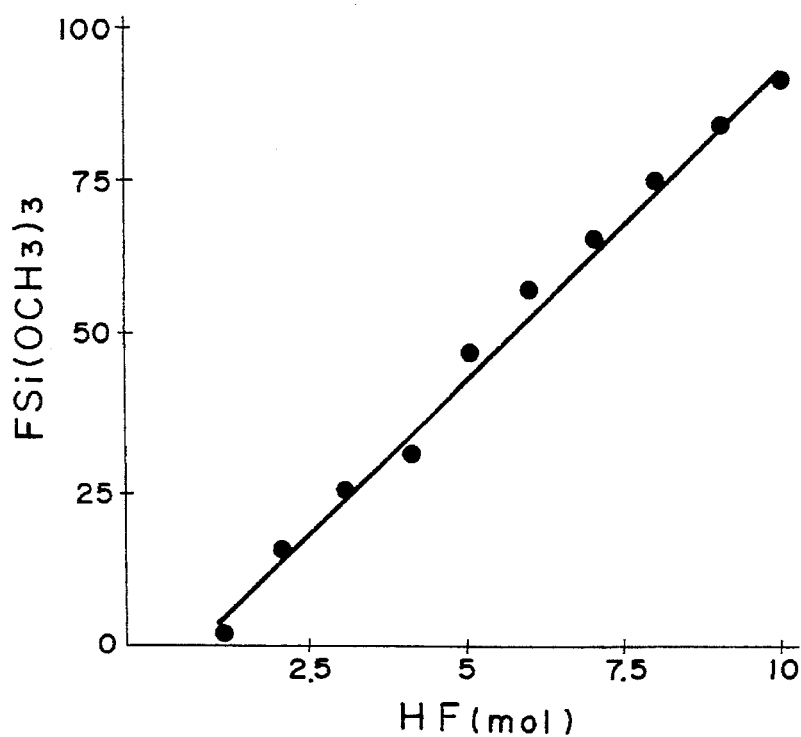
FIG. 3 is a graph showing the relation of quantity of HF consumption and FSi(OR)$_3$.

After completion of reaction to remove unreacted HF, the reaction vessel was heated (in the range of temperature from not less than boiling point of HF to not more than room temperature). At each supply of HF of approximate 1 mol, sampling was carried out and the situation of reaction was traced using gas chromatography. A measurement result till HF 10 mol is consumed completely is shown in FIG. 3. According to the FIG. 3, it was found that HF was not detected and the products consisted of trimethoxyfluorosilane and methanol. It was desirable to set the HF supply quantity larger than a theoretical value, because of partial thermal decomposition reaction.

Next, the refinement of trimethoxyfluorosilane obtained as above was carried out. That is, after removing methanol under normal pressure using a general refinement distillation device trimethoxyfluorosilane was distilled, and purity of the product was analyzed. As a result, the yield of product was 85%, and it agreed with the result that shown in FIG. 3.

What is claimed is:

1. A method of manufacturing FSi(OR)$_3$, comprising the steps of reacting Si(OR)$_4$ with HF, and purifying said FSi(OR)$_3$, wherein R is an alkyl group, a phenyl group, or an alkyl phenyl group.

2. A method of manufacturing FSi(OR)$_3$, comprising the steps of reacting a mixture consisting essentially of Si(OR)$_4$ and HF, wherein R is an alkyl group, a phenyl group, or an alkyl phenyl group.

3. The method of claim 2, further comprising the step of purifying said FSi(OR)$_3$.

4. The method of claim 1, wherein said reacting comprises blowing gaseous HF into liquid Si(OR)$_4$ at a temperature of not more than 0° C.

5. The method of claim 1, wherein said HF is present in a molar amount greater than the molar amount of said Si(OR)$_4$.

6. The method of claim 4, wherein said reacting step produces a product, and said method further comprises heating said product to a temperature of from the boiling point of HF to room temperature prior to said purifying step.

7. The method of claim 2, wherein said reacting step produces a product, and said method further comprises heating said product to a temperature of from 19° C. to 25° C. after said reacting step.

8. The method of claim 1, wherein R is an alkyl group.

9. The method of claim 8, wherein R is selected from the group consisting of CH$_3$, C$_2$H$_5$, C$_3$H$_7$, C$_4$H$_9$, C$_5$H$_{11}$, C$_{12}$H$_{25}$, C$_{14}$H$_{29}$ and C$_{16}$H$_{33}$.

10. The method of claim 1, wherein R is a phenyl group.

11. The method of claim 1, wherein R is an alkylphenyl group.

12. The method of claim 11, wherein R is selected from the group consisting of phenyl-substituted CH$_3$, C$_2$H$_5$, C$_3$H$_7$, C$_4$H$_9$, C$_5$H$_{11}$, C$_{12}$H$_{25}$, C$_{14}$H$_{29}$ and C$_{16}$H$_{33}$.

13. The method of claim 1, wherein said reacting comprises adding successive 10% molar portions of HF relative to the molar amount of Si(OR)$_4$ until no HF is detected in the reaction mixture.

* * * * *

UNITED STATES PATENT AND TRADEMARK OFFICE
CERTIFICATE OF CORRECTION

PATENT NO. : 5,468,894
DATED : November 21, 1995
INVENTOR(S) : Ryuichi YAMAGUCHI, et al.

It is certified that error appears in the above-indentified patent and that said Letters Patent is hereby corrected as shown below:

Column 1, line 21, "close each" should read --close to each--;
　　　　　line 56, "poisonoum" should read --poisonous--.
Column 2, line 12, "than" should read -- than 0°C.--;
　　　　　line 30, "poisonoum" should read --poisonous--;
　　　　　line 56, "tool" should read --mol--.

Signed and Sealed this

Twenty-fourth Day of September, 1996

Attest:

BRUCE LEHMAN

Attesting Officer　　　Commissioner of Patents and Trademarks